United States Patent [19]
Narui et al.

[11] Patent Number: 5,094,851
[45] Date of Patent: Mar. 10, 1992

[54] WATER-CONTAINING EXTERNAL PREPARATIONS

[75] Inventors: Takashi Narui, Sakura; Tetsuo Kaneko, Narita; Katsumi Imamori; Akira Iwasa, both of Yotsukaido, all of Japan

[73] Assignee: SS Pharmaceutical Co., Ltd., Tokyo, Japan

[21] Appl. No.: 577,568

[22] Filed: Sep. 5, 1990

[51] Int. Cl.$^5$ .................................................. A61K 6/00
[52] U.S. Cl. ..................................... 514/179; 424/47; 424/59; 424/63
[58] Field of Search ............... 424/401, 47, 78, 59, 424/63

[56] References Cited

U.S. PATENT DOCUMENTS

| | | | |
|---|---|---|---|
| 3,639,434 | 1/1972 | Oxley et al. | 260/397.45 |
| 3,906,108 | 9/1975 | Felty | 514/560 |
| 4,124,707 | 11/1978 | Green et al. | 424/241 |
| 4,214,000 | 7/1980 | Papa | 514/494 |
| 4,294,852 | 10/1981 | Wildnauer | 514/557 |

FOREIGN PATENT DOCUMENTS 0042827 12/1981 European Pat. Off. .
0280737 9/1988 European Pat. Off. .
6137 6/1968 France .

*Primary Examiner*—Thurman K. Page
*Assistant Examiner*—Louis A. Piccone
*Attorney, Agent, or Firm*—Oblon, Spivak, McClelland, Maier & Neustadt

[57] ABSTRACT

Water-containing external preparations are disclosed, which contain, as essential ingredients, (a) 0.05-1 wt. % of deprodone propionate and (b) 1-20 wt. % of a polyhdric alcohol.

4 Claims, 2 Drawing Sheets

WATER-CONTAINING EXTERNAL PREPARATIONS

BACKGROUND OF THE INVENTION

1) Field of the Invention

The present invention relates to water-containing external preparations which contain corticosteroid, and more specifically to water-containing external preparations which contain deprodone propionate as an effective ingredient, can exhibit its effects to the maximum extent and over a prolonged period of time, do not have skin irritation, and are physicochemically stable.

2) Description of the Related Art

Corticosteroids have heretofore been employed widely as remedial agents in the field of dermatology because they exhibit even in a small amount strong therapeutic effects for inflammatory and allergic skin diseases and have fastacting property compared with other medicaments.

The corneum in the surface of the skin however inherently functions as a barrier in order to prevent penetration of foreign substances from the outside into the body. This has led to the problem that sufficient percutaneous absorption cannot be achieved with an external preparation containing a corticosteroid ingredient simply mixed in a base which has conventionally been employed in external preparations.

To improve this problem, various percutaneous absorption promoters such as 1-dodecylazacycloheptan-2-one, dimethylsulfoxide and dimethylformamide have been used in recent years. These promoters are however not considered sufficient in safety and feeling of use.

It is also practiced to use a corticosteroid having strong effects so as to tentatively improve the percutaneous absorption or to increase the concentration of a corticosteroid so as to increase the therapeutic effects. These methods are however accompanied by the problem of side effects because the influence to the whole body or a part thereof increases in proportion to the effects and concentration of the corticosteroid.

It has therefore been desired to develop a corticosteroid-containing ointment which has high curative effects and which gives less side effects to the whole body or a part thereof and has higher safety.

It is however to be noted that the curative effects of an external preparation significantly vary depending on the kind of its base and the like even when the external preparation contains the same effective ingredient at the same concentration and an external preparation having excellent curative effects and little side effects can be obtained for the first time when its effective ingredient and its base match well in physicochemical properties.

SUMMARY OF THE INVENTION

Under such circumstances, the present inventors have carried out an extensive investigation on the relationship between individual corticosteroids and bases. As a result, it has been found that the incorporation of deprodone propionate represented by a formula, which is to be described hereinafter, along with water and a polyhydric alcohol can provide an external preparation which allows deprodone propionate to exhibit its effects to the maximum extent and over a prolonged period of time, does not have side effects such as skin irritation, and is physicochemically stable, leading to the completion of the present invention.

In one aspect of the present invention, there is thus provided a water-containing external preparation comprising, as essential ingredients, the following two ingredients (a) and (b):

(a) 0.05-1 wt.% of deprodone propionate; and
(b) 1-20 wt.% of a polyhydric alcohol.

The preparation may be in the form of a cream for external use. In addition to the ingredients (a) and (b), the cream further comprises 5-45 wt.% of an oily ingredient comprising one or more of white petrolatum, cetanol, diisopropyl adipate, crotamiton and almond oil, 2-10 wt.% of a nonionic surfactant and 45-85 wt.% of water.

The preparation may also be in the form of a lotion. In addition to the ingredients (a) and (b), the lotion further comprises 0.1-1.5 wt.% of a suspending agent.

The water-containing external preparation of the present invention, which contains the corticosteroid, physicochemically remains stable even when stored over a long period of time, does not have skin irritation and side effects, and exhibits superb curative effects.

The cream can give long-lasting curative effects because its oily ingredient and polyhydric alcohol reduce transpiration of water from the skin to protect the skin and also enhance the percutaneous absorption to increase the retention of the medicament in the skin.

The polyhydric alcohol also contributes to the stabilization of the emulsified state of the cream.

By adjusting the pH of the cream to 3.5-6.5, i.e., to mild acidity close to the skin pH, skin irritation can be reduced and the stability of deprodone propionate, the curative ingredient, can be enhanced.

By adjusting the pH of the lotion to mild acidity close to the skin pH, skin irritation can also be reduced. In addition, the stability of deprodone propionate, the curative ingredient, can be enhanced.

DETAILED DESCRIPTION OF THE INVENTION AND PREFERRED EMBODIMENTS

Figure 1:
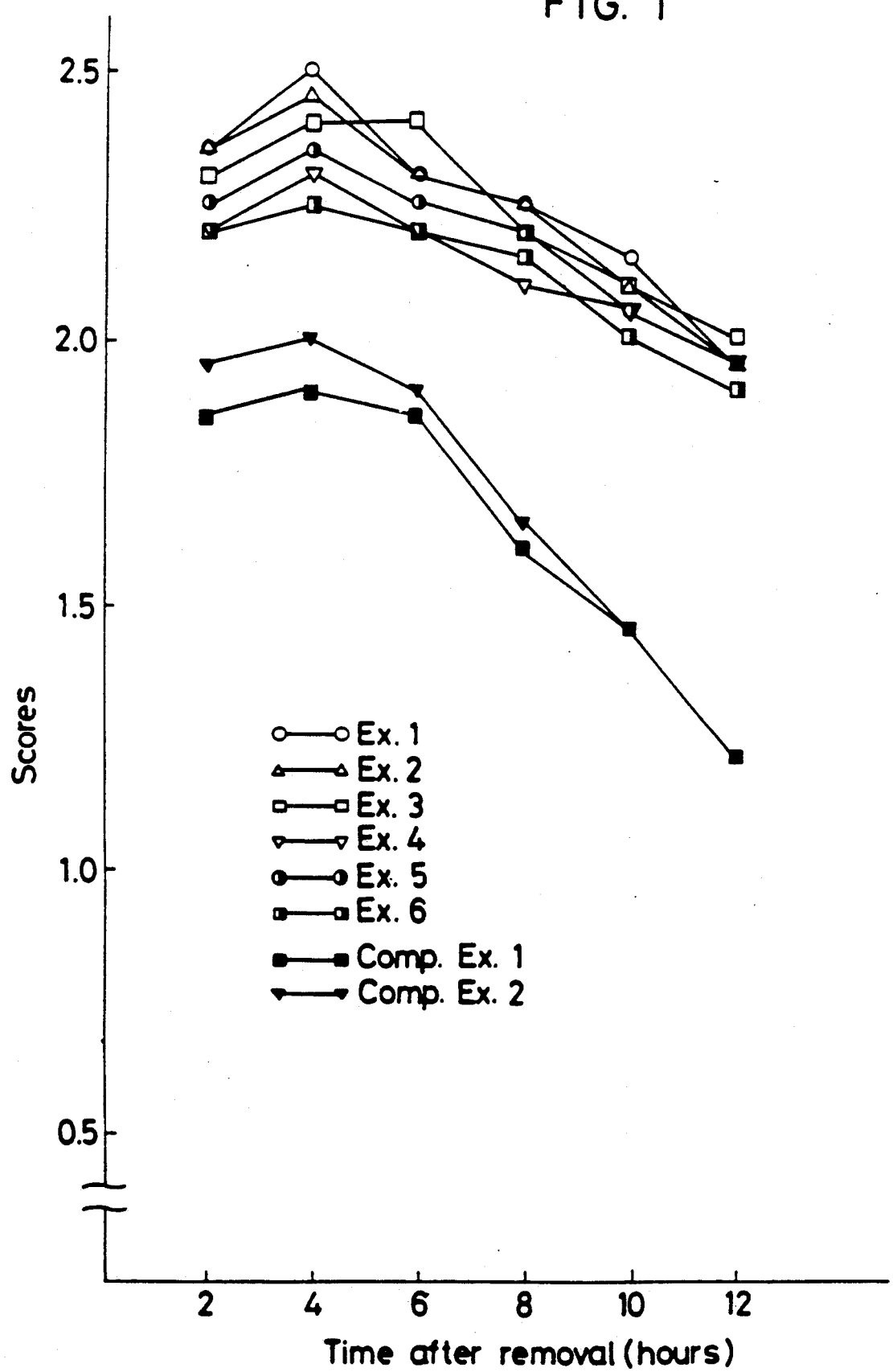
FIG. 1 diagrammatically illustrates the results of a vasoconstriction test of the creams of Examples 1-6 and Comparative Examples 1-2.

The term "water-containing external preparation" as used herein means an external preparation which contains even water as an ingredient thereof. Specific exemplary preparation forms can include creams, lotions and the like.

Deprodone propionate, ingredient (a) in the present invention, is a compound which is obtained by esterifying with propionic acid the 17-position of the prednisolone skeleton and deoxidating its 21-position and has the structure represented by the following formula:

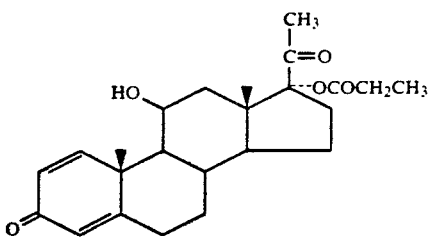

Ingredient (a) is added in an amount of 0.05-1 wt. % (hereinafter indicated merely by "%"), preferably 0.1-0.5%, both based on the whole composition.

Examples of the polyhydric alcohol as ingredient (b) in the present invention include glycerin, sorbitol, sorbitan and glycols. Among these, it is preferred to use either one of propylene glycol, 1,3-butylene glycol and polyethylene glycols having an average molecular weight of 200-6,000. Ingredient (b) can be added in an amount of 1-20% based on the whole composition.

Upon formulation of the water-containing external preparation of the present invention, various ingredients suitable for individual preparations can be added further besides the two essential ingredients described above.

When a cream-like preparation is formulated by way of example, it is preferred to add an oily ingredient, a nonionic surfactant and water besides the two ingredients (a) and (b).

Exemplary oily ingredients which can be suitably added include those containing one or more of white petrolatum, cetanol, diisopropyl adipate, crotamiton and almond oil. These oily ingredients can be added preferably in an amount of 2-15% for white petrolatum, 2-15% for cetanol, 0.5-10% for diisopropyl adipate, 0.1-5% for crotamiton, and 1-10% for almond oil, all based on the whole composition.

In addition to the preferred oily ingredients described above, one or more of oily ingredients generally employed in cream-like preparations can also be incorporated as needed. Examples of such oily ingredients include liquid and solid hydrocarbons such as liquid paraffin, paraffin and squalane; solid higher alcohols such as stearyl alcohol; fatty acids such as stearic acid and oleic acid; esters such as isopropyl myristate and diethyl sebacate; waxes such as white beeswax and lanolin; and liquid oils and fats such as peanut oil.

On the other hand, illustrative of the non-ionic surfactant include sorbitan fatty acid esters, glycerin fatty acid esters, polyoxyethylene sorbitan fatty acid esters, polyoxyethylene alkyl ethers, polyethylene glycol fatty acid esters, and polyglycerin fatty acid esters. Described specifically, there are sorbitan monooleate, sorbitan monostearate, glycerin monostearate, polyoxyethylene sorbitan monostearate, polyoxyethylene cetyl ether, polyethylene glycol monostearate, and decaglycerin pentaoleate.

Upon formulation of a cream-like preparation, there are incorporated – in addition to 0.05-1%, preferably 0.1-0.5% of ingredient (a), 1-20%, preferably 2-10% of ingredient (b), 5-45%, preferably 10-35% of an oily ingredient, 1-15%, preferably 2-10% of a non-ionic surfactant, and 45-85% of water, all based on the composition. It is preferable to formulate the cream-like preparation in such a way that its final pH is adjusted to 3.5-6.5 with a buffer commonly employed in external preparations, such as a citrate buffer.

It is also preferable to add a stabilizer upon formulation of the cream-like preparation described above. Usable exemplary stabilizers include antioxidants such as butylhydroxyanisole and dibutylhydroxytoluene (BHT); and antiseptics such as parahydroxybenzoate esters and dehydroacetic acid.

Upon formulation of a lotion-like preparation, it is preferable to add a suspending agent besides ingredients (a) and (b).

Exemplary suspending agents include carboxyvinyl polymer, hydroxypropylcellulose, methylcellulose, and polyvinylpyrrolidone. Use of carboxyvinyl polymer is particularly preferred. Commercial carboxyvinyl polymers can be used, including, for example, "Carbopol 934", "Carbopol 940" and "Carbopol 941" (trade names; products of B. F. Goodrich Chemical Co.); and "HIVISWAKO 103", "HIVISWAKO 104" and "HIVISWAKO 105" (trade names; products of Wako Pure Chemical Industries, Ltd.).

Upon formulation of a lotion-like preparation, it is preferable to use, as a suspending agent, carboxyvinyl polymer and hydroxypropylcellulose in combination. Hydroxypropylcellulose acts to promote the formation of a protective film for the skin. Commercial products can be employed, including, for example, "HPC-M" and "HPC-H" (trade names; products of Nippon Soda Co., Ltd.).

When a lotion-like preparation is formulated, it is preferable to use, as ingredient (a), crystals or powder having an average particle size not greater than 10μm. This is to enhance its adhesion to the skin by making the particles smaller, whereby the percutaneous absorption can be promoted and the retention in the skin can be increased. When the above-described suspending agent is used in combination with ingredient (a), fine particles of deprodone propionate as ingredient (a) can be maintained in a stably suspended state owing to the thickening action of the suspending agent. In addition, after transpiration of water from the solvent, a thin film is formed on the skin to protect the latter and further to enhance the adhesion of the fine particles of deprodone propionate to the skin, so that the percutaneous absorption is assisted and the retention in the skin can be increased.

Ingredient (b) serves inter alia to assist the dispersion of fine particles of ingredient (a), to prevent agglomeration of the fine particles themselves and to retard transpiration of water, so that ingredient (b) can enhance the percutaneous absorption.

A lotion-like preparation can be formulated by adding 0.05-1%, preferably 0.1-0.5% of ingredient (a), 1-10%, preferably 2-5% of ingredient (b), and .01-1.5% of a suspending agent. It is preferable that 0.1-1%, especially 0 3-0.6% of hydroxypropylcellulose, based on the whole composition, is incorporated as a suspending agent.

To the lotion-like preparation, polyoxyethylene hydrogenated castor oil, polyoxyethylene sorbitan fatty acid ester or an alkyl sulfate can be added as a dispersing agent in an amount of 0.02-0.2% based on the whole composition as needed.

It is preferable to adjust the viscosity of the above lotion-like preparation to 30-200 cps, especially to 50-100 cps. It is also preferable to adjust the final pH of the preparation to 3.5-6.5, notably to 4.0-5.0. For such a pH adjustment, sodium benzoate, sodium hydroxide or the like can be used by way of example.

The present invention will hereinafter be described in further detail by the following examples, comparative examples and tests.

EXAMPLE 1

(Composition)

Deprodone propionate: 0.3 g
Cetanol: 5.0 g
White petrolatum: 7.0 g
Crotamiton: 1.0 g
Propylene glycol: 5.0 g
Glycerin monostearate: 5.0 g
Polyoxyethyelene(25) cetyl ether: 2.5 g
Methyl parahydroxybenzoate: 0.2 g
Butyl parahydroxybenzoate: 0.1 g
BHT: 0.02 g
Buffer: As needed
Purified water: Sufficient to produce 100 g (Formulation method)

The oil-phase ingredients were melted at 60–70° C. Propylene glycol in which deprodone propionate had been dissolved was then added to the melt, followed by stirring. Purified water with the buffer dissolved therein was added at 70–80° C. After emulsification, the emulsion was cooled to room temperature so that a cream for external application was formulated.

EXAMPLE 2

(Composition)

Deprodone propionate: 0.3 g
Cetanol: 4.0 g
White petrolatum: 14.5 g
Diisopropyl adipate: 1.0 g
Crotamiton: 1.0 g
Propylene glycol: 10.0 g
Glycerin monostearate: 3.0 g
Polyoxyethyelene(25) cetyl ether: 1.5 g
Methyl parahydroxybenzoate: 0.2 g
Butyl parahydroxybenzoate: 0.1 g
BHT: 0.02 g
Buffer: As needed
Purified water: Sufficient to produce 100 g (Formulation method)

In a similar manner to Example 1, a cream for external application was formulated.

EXAMPLE 3

(Composition)

Deprodone propionate: 0.3 g
Cetanol: 8.0 g
White petrolatum: 10.0 g
Diisopropyl adipate: 3.0 g
Propylene glycol: 10.0 g
Glycerin monostearate: 5.0 g
Polyoxyethyelene(25) cetyl ether: 2.5 g
Methyl parahydroxybenzoate: 0.2 g
Butyl parahydroxybenzoate: 0.1 g
BHT: 0 02 g
Buffer: As needed
Purified water: Sufficient to produce 100 g (Formulation method)

In a similar manner to Example 1, a cream for external application was formulated.

EXAMPLE 4

(Composition)

Deprodone propionate: 0.3 g
Cetanol: 8.0 g
White petrolatum: 10.0 g
Diisopropyl adipate: 3.0 g
1,3-Butylene glycol: 10.0 g
Glycerin monostearate: 5.0 g
Polyoxyethyelene(25) cetyl ether: 2.5 g
Methyl parahydroxybenzoate: 0.2 g
Butyl parahydroxybenzoate: 0.1 g
BHT: 0.02 g
Buffer: As needed
Purified water: Sufficient to produce 100 g (Formulation method)

In a similar manner to Example 1, a cream for external application was formulated.

EXAMPLE 5

(Composition)

Deprodone propionate: 0.3 g
Cetanol: 7.5 g
Almond oil: 10.0 g
Glycerin monostearate: 5.0 g
Polyoxyethyelene(25) cetyl ether: 2.5 g
Propylene glycol: 10.0 g
Methyl parahydroxybenzoate: 0.2 g
Butyl parahydroxybenzoate: 0.1 g
BHT: 0.02 g
Buffer: As needed
Purified water: Sufficient to produce 100 g (Formulation method)

In a similar manner to Example 1, a cream for external application was formulated.

EXAMPLE 6

(Composition)

Deprodone propionate: 0.3 g
Stearyl alcohol: 6.0 g
White petrolatum: 7.0 g
Propylene glycol: 5.0 g
Glycerin monostearate: 5.0 g
Polyoxyethyelene(25) cetyl ether: 2.5 g
Methyl parahydroxybenzoate: 0.2 g
Butyl parahydroxybenzoate: 0.1 g
BHT: 0.02 g
Buffer: As needed
Purified water: Sufficient to produce 100 g (Formulation method)

In a similar manner to Example 1, a cream for external application was formulated.

COMPARATIVE EXAMPLE 1

(Composition)

Deprodone propionate: 0.3 g
Stearyl alcohol: 7.5 g
Isopropyl myristate: 5.0 g
Glycerin monostearate: 5.0 g
Polyoxyethyelene(25) cetyl ether: 2.5 g
Methyl parahydroxybenzoate: 0.2 g
Propyl parahydroxybenzoate: 0.1 g
BHT: 0.005 g Buffer: As needed
Purified water: Sufficient to produce 100 g (Formulation method)

In a similar manner to Example 1, a cream for external application was formulated.

COMPARATIVE EXAMPLE 2

(Composition)

Deprodone propionate: 0.3 g
Stearyl alcohol: 10.0 g
Medium-chain-length fatty acid triglyceride: 5.0 g
Sorbitan monooleate: 3.0 g
Polyoxyl stearate 40: 3.0 g
Methyl parahydroxybenzoate: 0.2 g
Propyl parahydroxybenzoate: 0.1 g
BHT: 0.005 g
Buffer: As needed
Purified water: Sufficient to produce 100 g (Formulation method)

In a similar manner to Example 1, a cream for external application was formulated.

EXAMPLE 7

(Composition)

Deprodone propionate: 0.3 g
Propylene glycol: 3.0 g
Carboxyvinyl polymer: 0.2 g
Hydroxypropylcellulose: 0.4 g
Sodium benzoate: 0.1 g
Purified water: Sufficient to produce 100 g (Formulation method)

A dispersion of deprodone propionate in propylene glycol was added to an aqueous solution of carboxyvinyl polymer and hydropropylcellulose, followed by stirring. The remaining purified water was added to produce the total weight, whereby a lotion was formulated.

EXAMPLE 8

(Composition)

Deprodone propionate: 0.3 g
Propylene glycol: 2.0 g
Carboxyvinyl polymer: 0.4 g
Sodium benzoate: 0.1 g
Purified water: Sufficient to produce 100 g (Formulation method)

A lotion was formulated in a similar manner to Example 7.

EXAMPLE 9

(Composition)

Deprodone propionate: 0.3 g
Propylene glycol: 3.0 g
Carboxyvinyl polymer: 0.2 g
Hydroxypropylcellulose: 0.4 g
Sodium benzoate: 0.1 g
Polyoxyethylene(20) sorbitan monooleate: 0.1 g
Purified water: Sufficient to produce 100 g (Formulation method)

A lotion was formulated in a similar manner to Example 7.

Comparative Example 3

(Composition)

Deprodone propionate: 0.3 g
Isopropyl alcohol: 45.0 g
Citric acid: 0.3 g
Sodium citrate: As needed
Purified water: Sufficient to produce 100 g (Formulation method)

Deprodone propionate was dissolved in isopropyl alcohol Purified water in which citric acid and sodium citrate had been dissolved was then added to produce the total weight, whereby a lotion was formulated.

COMPARATIVE EXAMPLE 4

(Composition)

Deprodone propionate: 0.3 g
BHT: 0.02 g
Propylene glycol: Sufficient to produce 100 g (Formulation method)

Deprodone propionate and BHT were dissolved in a portion of propylene glycol. The remaining portion of propylene glycol was added to produced the total weight, whereby a lotion was formulated.

TEST 1

With respect to the creams obtained in Examples 1-6 and Comparative Examples 1-2, respectively, a vasoconstriction test was conducted on the normal human skin in an open system in accordance with the following testing method.

(Testing method)

An adhesive plaster (30 mm wide, 17 cm long, about 1 mm thick) through which holes having an internal diameter of 10 mm were formed was adhered to a lower middle back area of a volunteer. Each test cream was applied for 2 hours in two of the holes at a rate of 30 mg per hole. After the two-hour period, the test creams were removed. After 2, 4, 6, 8, 10 and 12 hours from the removal of the test ointments, the degrees or the presence or absence of skin paleness due to vasoconstriction were determined. Two points were given when marked paleness was observed, one point when apparent paleness was observed, 0.5 point when slight paleness was observed, and 0 point when no paleness was observed. Average of scores on 30 volunteers were determined. The results are diagrammatically shown in FIG. 1.

In the above test, the creams in which one or more of white petrolatum, cetanol, diisopropyl adipate, crotamiton and almond oil were used in combination with propylene glycol or 1,3-butylene glycol had a high score as shown in FIG. 1. It is hence envisaged that the effects of deprodone propionate were long-lasting.

In addition, bases prepared in accordance with the same compositions as Examples 1-6 and Comparative Examples 1-2 except for the omission of deprodone propionate were applied to lower middle back areas of 30 normal volunteers at two spots per base and volunteer. After 48 hours, the irritation of each base was observed. As is shown in Table 1, irritation was practically unobserved with respect to the bases of Examples 1-6.

Regarding physicochemical stability, the creams of the examples developed no problem in both discoloration and the stability of deprodone propionate.

TABLE 1

| Irritation Test of Bases | |
|---|---|
| Sample | Percent positive |
| Example 1 | 0/60 |
| Example 2 | 1/60 |
| Example 3 | 0/60 |
| Example 4 | 0/60 |
| Example 5 | 0/60 |
| Example 6 | 0/60 |
| Comparative Example 1 | 1/60 |
| Comparative Example 2 | 1/60 |

TABLE 2

Physicochemical Stability (Observation after 6 Months)

| | Discoloration* | | | Content, % | | |
|---|---|---|---|---|---|---|
| | Storage conditions | | | | | |
| Item observed Sample | Room temperature. | 45° C. | 1000 lux | Room temperature | 45° C. | 1000 lux |
| Example 1 | − | − | − | 99.9 | 98.8 | 97.3 |
| Example 2 | − | − | − | 100.1 | 99.0 | 98.7 |
| Example 3 | − | − | − | 99.6 | 99.3 | 98.1 |
| Example 4 | − | − | − | 99.8 | 98.7 | 97.2 |
| Example 5 | − | − | − | 99.5 | 98.9 | 97.4 |
| Example 6 | − | − | − | 101.1 | 99.0 | 96.8 |
| Comparative Example 1 | − | − | − | 99.7 | 98.5 | 96.4 |
| Comparative Example 2 | − | − | ± | 100.3 | 98.7 | 95.6 |

*Discoloration: − no discoloration, ± some discoloration, + apparent discoloration.

Regarding physicochemical stability, the lotions of Examples 7-9 developed no problem as shown in Table 4.

TABLE 3

| Irritation Test of Bases | |
|---|---|
| Sample | Percent positive |
| Example 7 | 0/60 |
| Example 8 | 1/60 |
| Example 9 | 0/60 |
| Comparative Example 3 | 5/60 |
| Comparative Example 4 | 1/60 |

TABLE 4

Physicochemical Stability (Observation after 6 Months)

| | Discoloration* | | | Viscosity** | | | Content, % | | |
|---|---|---|---|---|---|---|---|---|---|
| | Storage conditions | | | | | | | | |
| Item observed Sample | Room temp. | 45° C. | 1000 lux | Room temp. | 45° C. | 1000 lux | Room temp. | 45° C. | 1000 lux |
| Example 7 | − | − | − | 70 | 80 | 65 | 100.3 | 100.4 | 95.6 |
| Example 8 | − | − | − | 65 | 70 | 63 | 99.8 | 100.1 | 96.4 |
| Example 9 | − | − | − | 75 | 82 | 68 | 99.7 | 99.9 | 96.5 |
| Comparative Example 3 | − | − | − | / | / | / | 99.6 | 99.7 | 92.3 |
| Comparative Example 4 | − | − | − | / | / | / | 99.5 | 99.8 | 96.4 |

*Discoloration: − no discoloration, ± some discoloration, + apparent discoloration.
**Viscosity: Measured at 25° C. and 100 rpm for 1 minute by E-type viscometer equipped with standard cones.

TEST 2

With respect to the lotions obtained in Examples 7-9 and Comparative Examples 3-4, respectively, a vasoconstriction test was conducted on the normal human skin in an open system in a similar manner to Test 1. The results are diagrammatically shown in FIG. 2.

Figure 2:
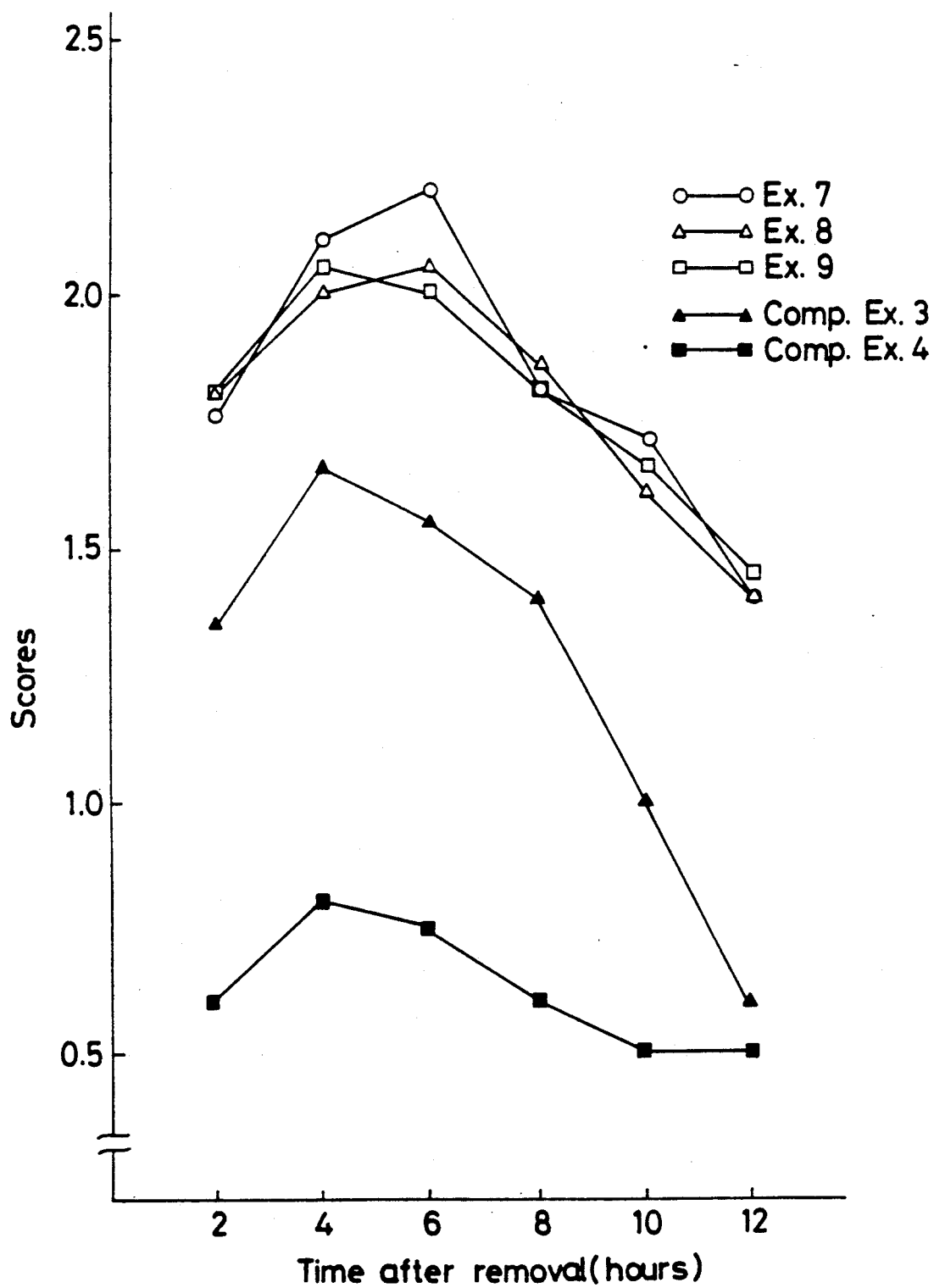
FIG. 2 diagrammatically shows the results of a vasoconstriction test of the lotions of Examples 7-9 and Comparative Examples 3-4.

In the above test, the lotions in which a suspending agent was used along with a suitable amount of propylene glycol had a high score as shown in FIG. 2. It is hence envisaged that the effects of deprodone propionate were longlasting.

In addition, bases prepared in accordance with the same compositions as Examples 7-9 and Comparative Examples 3-4 except for the omission of deprodone propionate were tested with respect to their irritation in a similar manner to Test 1. As shown in Table 3, irritation (slight erythema) was observed with respect to the base of Comparative Example 3, but similar irritation was practically unobserved with respect to the bases of Examples 7-9.

What is claimed is:

1. A water-containing preparation for external use consisting essentially of ingredients (a) and (b):
   (a) 0.05-1 wt. % of deprodone propionate; and
   (b) 1-20 wt. % of a polyhydric alcohol selected from the group consisting of propylene glycol, 1,3-butylene glycol, polyethylene glycols having an average molecular weight of 200-6,000, glycerin, sorbitol and sorbitan.

2. The preparation of claim 1, wherein the preparation is in the form of a cream; and in addition to the ingredients (a) and (b), the preparation further comprises 5-45 wt. % of an oily ingredient selected from the group consisting of white petrolatum, cetanol, diisopropyl adipate, crotamiton, almond oil and mixtures thereof, 2-10 wt. % of a non-ionic surfactant and 45-85 wt. % of water.

3. The preparation of claim 1, wherein the preparation is in the form of a lotion; and in addition to 0.05-1 wt. % of the ingredient (a) and 1-10 wt. % of the ingredient (b), the preparation further comprises 0.1-1.5 wt. % of a suspending agent.

4. The preparation of claim 3, wherein a carboxyvinyl polymer and hydroxpropylcellulose are used in combination as the suspending agent.

* * * * *